United States Patent [19]
Sneider

[11] 3,986,509
[45] Oct. 19, 1976

[54] DISPOSABLE VAGINAL DOUCHE SYRINGE

[76] Inventor: Vincent R. Sneider, 3422 Hallcrest Drive, NE., Atlanta, Ga. 30319

[22] Filed: June 26, 1975

[21] Appl. No.: 590,590

[52] U.S. Cl............................... 128/232; 128/251
[51] Int. Cl.²......................................... A61M 1/00
[58] Field of Search .......... 128/251, 247, 232, 230, 128/224, 239; 215/11; 222/92, 96, 106, 107, 566

[56] References Cited
UNITED STATES PATENTS

| 764,996 | 7/1904 | Ellis | 128/232 X |
| 2,782,784 | 2/1957 | Ritter | 128/232 |
| 3,354,883 | 11/1967 | Southerland | 128/232 |
| 3,589,362 | 6/1971 | Zamarra | 128/251 X |
| 3,773,047 | 11/1973 | Sneider | 128/232 |

Primary Examiner—John D. Yasko
Attorney, Agent, or Firm—Jones, Thomas & Askew

[57] ABSTRACT

A disposable vaginal douche syringe including a nozzle portion, a disposable bag portion and a valve member for selective flow of fluid from the bag through the nozzle. The nozzle portion is constructed so that the nozzle may pivot for convenience in use.

5 Claims, 7 Drawing Figures

DISPOSABLE VAGINAL DOUCHE SYRINGE

This invention relates to vaginal douche syringes and is more particularly concerned with a convenient sanitary syringe having a replaceable bag member and a selectively openable valve member.

Vaginal douche syringes which are designed to hold a substantial quantity of liquid are well known in the art, and have achieved wide acceptance commercially. Furthermore, there is currently a large market for syringes that are packaged in a sterile condition for one-time use, to be discarded thereafter. As is usual, however, there is some difficulty in providing a syringe which is inexpensive while also being of sufficient quality to be used for its intended purpose.

One recent development is a syringe in which a flexible bag is used as the body of the syringe, the bag being removable for discarding after use, see U.S. Pat. No. 3,773,047. Since the bag of this device has almost no rigidity of its own, it is extremely easy to dispense the liquid before one is ready to dispense the liquid simply by inadvertently grasping and squeezing the filled bag. In such case, the liquid is despensed inadvertently and is wasted rather than being put to use. In addition, it is possible for the bag to become dislodged from the nozzle portion while in use.

The syringe of the present invention overcomes the above-mentioned and other difficulties by providing in one embodiment a cap member for holding a flexible bag and for securely clamping the bag by a wedging action to prevent inadvertent removal thereof. The cap member in another embodiment carries a nozzle, through which a liquid may be discharged, and includes valve means between the cap member and the nozzle for selectively allowing liquid to be discharged through the nozzle. The particular arrangement is such that a single cap member may be utilized, and a plurality of different nozzles may be used in conjunction with the cap without losing any of the advantages and features of the invention.

These and other features and advantages of the present invention will become apparent on consideration of the following specification when taken in conjunction with the accompanying drawings in which.

Figure 1:
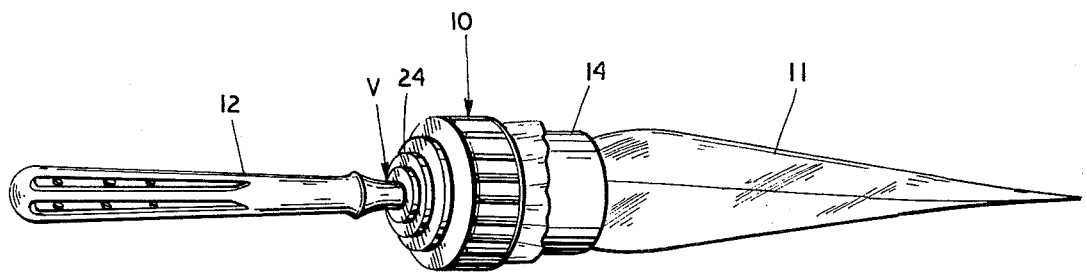
FIG. 1 is a perspective view of one form of syringe made in accordance with the present invention.

Referring now more particularly to the drawings, and to those embodiments of the invention here chosen by way of illustration, it will be seen that the syringe shown in FIG. 1 of the drawings includes the cap member generally designated at 10, the cap 10 carrying a flexible bag 11 and a nozzle 12 thereon. The nozzle 12 here shown by way of illustration is a nozzle designed particularly for a vaginal douche; however, it will be understood by those skilled in the art that other forms of nozzles may be used equally well, as will become more apparent from the following discussion.

The cap member 10 mates with a tubular body 14 having threads 15 adjacent to one end thereof, the threads 15 encircling the end of the body 14 but stopping short of the extreme end 17. For cooperation with the threads 15, the cap member 10 has internal threads 18 designed to mate with the threads 15. The cap member 10 has an outer flange 19 in which the threads 18 are formed; and, there is an inner complementary flange 20 concentric with and spaced inwardly from the outer flange 19.

Figures 3, 4:
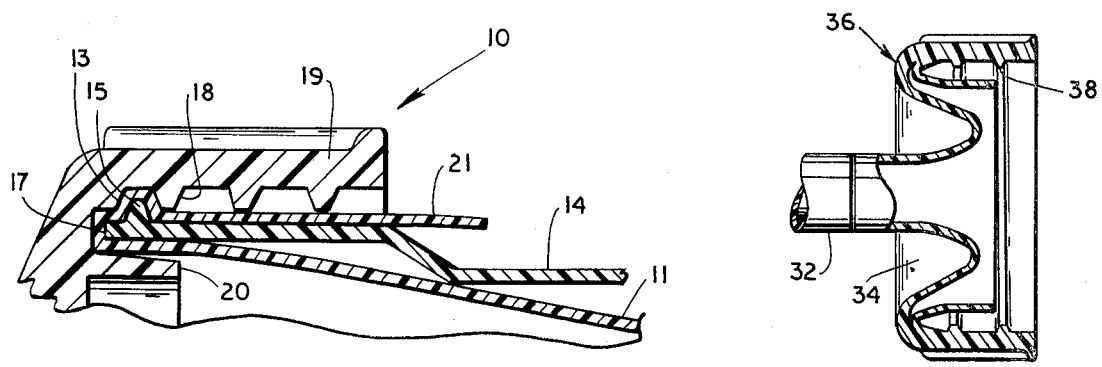
FIG. 3 is an enlarged detail cross-sectional view showing one form of clamping means for the flexible bag.
FIG. 4 is an elevational view, partially in cross-section, showing a modified form of cap for use in conjunction with the present invention.

As is best shown in FIG. 3 of the drawings, inner flange 20 cooperates with a ledge 13 formed adjacent threads 18 to provide a groove within which the end 17 of body 14 may be grasped. Flange 20 extends for a length sufficient to provide adequate sealing between the cap, the body 14 and any bag 11 positioned therebetween.

It should now be understood that body 14 is adapted to be inserted between the inner flange 20 and the outer flange 19 so that the threads 15 on the body 14 engage the threads 18 on the outer flange 19. The body 14 is then rotated, and the threads urge the end 17 of the body 14 into the groove between the flange 20 and the ledge 13. An important feature of this arrangement is that the flexible bag 11 is passed through the central opening of body 14, and the upper edge 21 of the flexible bag 11 is folded outwardly, passing over the end 17 to overlie threads 15 of body 14. With the bag so arranged the cap member 10 is placed over the end of body 14 so that the end of body 14, along with the upper portion of the bag 11, is inserted into the space between the inner flange 20 and the outer flange 19. As the threads urge the body 14 inwardly during rotation, the upper portion of the bag 11 is forced into the groove so that the bag 11 is urged against body 14 by the inner flange 20 and by the ledge 13. It will therefore be seen that bag 11 is firmly held to the cap member 10 by this arrangement; there is little chance of inadvertent removal of the bag 11 from the cap.

Figure 2:
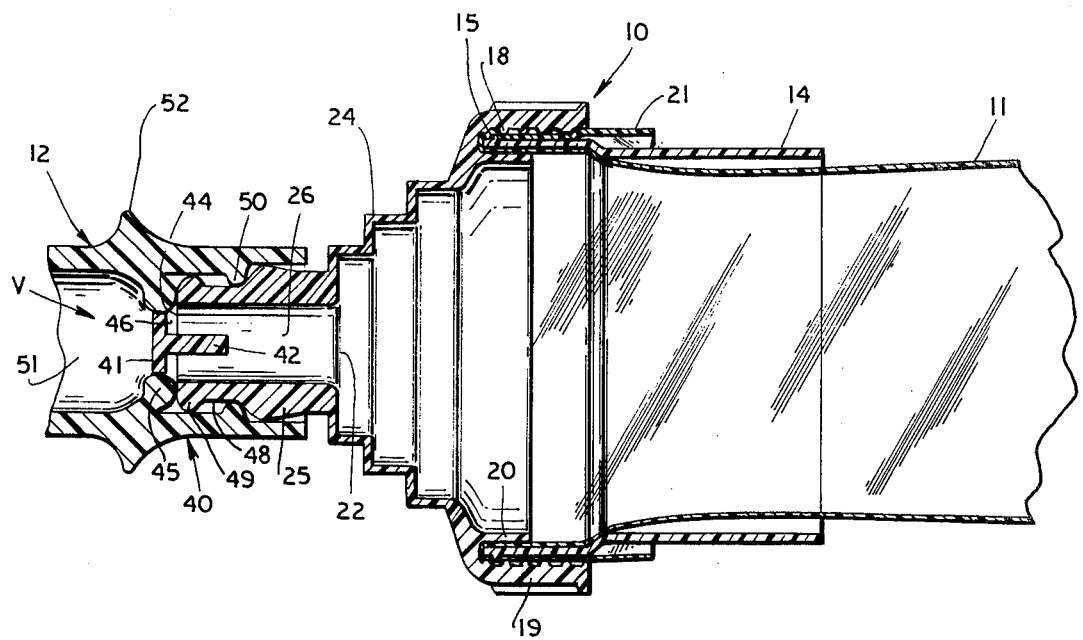
FIG. 2 is an enlarged longitudinal cross-sectional view through the syringe of FIG. 1, portions thereof being broken away.

The cap 10 includes a central opening 22 concentric with, and in communication with, the opening in the tubular body 14. The flange 19, previously described, is somewhat rigid in order to secure bag 11 to body 14; however, it is desirable to have a certain amount of flexibility available in a syringe so that the center line of the nozzle 12 can be displaced from the center line of the cap member 10 for convenience in use of the syringe. One means for allowing such displacement, or misalignment, is shown in FIG. 2 and includes a stepped transition section 24, the larger end of the transition section 24 being secured to, or formed as an extension of, the cap member 10. The smaller end of the transition section 24, terminating in a valve portion 25 of a valve V. The valve portion 25 has a central opening 26 therethrough, for discharge of liquid from bag 11.

Referring now to FIG. 4 of the drawings, in an optional embodiment there is provided a modified form of cap 10, the modified form being designated as 36. Modified cap 36 includes threads 38 for engagement with a body such as the body 14. Cap 36 includes a nozzle 32 and this nozzle is connected to the cap by means of a flexible web 34. As shown in cross-section, the web 34 has a sine curve shape, but it should be understood that the primary purpose of the shape of the flexible web 34 is to provide sufficient material and flexibility to allow the nozzle 32 to be angled with respect to the centerline of the cap 36.

Returning now to FIG. 2 of the drawings, attention is directed to the valve V where is will be seen that the valve portion 25 mates in male-female relationship with nozzle extension 40, extension 40 being formed integrally with the nozzle 12. Valve portion 25 includes a central disc 41 which is mounted to portion 25 concentrically with central opening 26 by means of web 42. The disc 41 is spaced apart from the end 44 of the valve portion 25, and is sightly smaller in diameter than the inside diameter of central opening 26 to provide an annular slot 46 for passage of liquid. This arrangement allows fluid to pass through central opening 26, and out of valve portion 25 by passing around the disc 41 and through slot 46.

Nozzle extension 40 includes a sealing bead 45 on its inside wall, and the sealing bead is dimensioned to engage the end 44 of valve portion 25 and disc 41 at one position of the extension so that the entire annular slot 46 through which fluid may flow is effectively closed and the valve V is closed.

In order to open the valve V, the nozzle extension is moved longitudinally thereby moving sealing bead 45 longitudinally away from the end 44 of the valve portion 25. Longitudinal movement of extension 40 is accomplished through a cooperating arrangement between ring 50 on the inner surface of extension 40 and neck 48 on valve portion 25. Neck 48 terminates in shoulder 49 and as extension 40 is moved longitudinally, ring 50 travels longitudinally along the surface of neck 48. This movement is sufficient to position the sealing bead 45 away from the slot 46 so that fluid may pass from central opening 26, through the slot 46 and into a central opening 51 in the nozzle 12. In order to facilitate movement of extension 40, there is a flange 52 surrounding the exterior of extension 40 to provide a convenient finger grip for movement thereof.

Tubular member 14 is constructed so that its overall length is significantly less than the installed length of bag 11. Normally, member 14 should be less than one-half the installed length of bag 11. In this fashion, bag 11 may be squeezed, when used to pump liquid from the bag and out of nozzle 12.

Other similar valves known in the prior art may be used with the syringe of the present invention, the valve here shown being chosen simply by way of illustration. Due to the structural arrangement of the valve V, it will be seen by those skilled in the art that a plurality of styles and designs of nozzle 12 may be provided, each with valve extension 40 formed integrally therewith. When valve V is made of a plastic material, for example, the valve extension 40 may be snapped off the valve portion 25 by forcing ring 50 over shoulder 49 so that nozzle 12 may be changed as desired.

Figure 5:
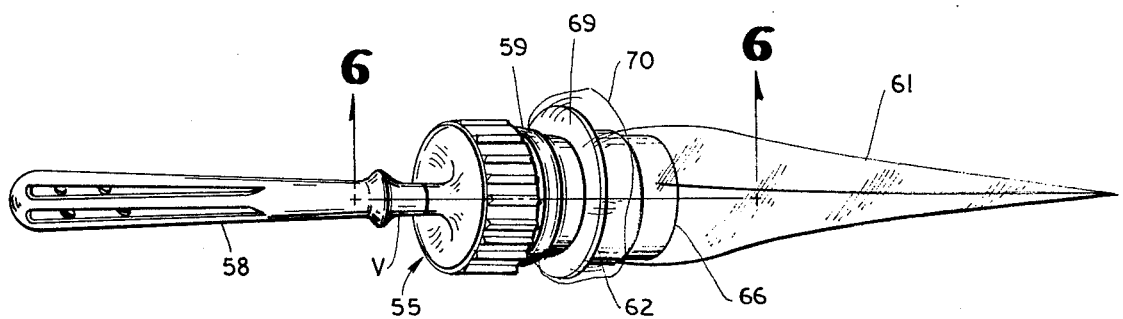
FIG. 5 is a view similar to FIG. 1 showing a modified form of clamping means for the flexible bag.
Figure 6:
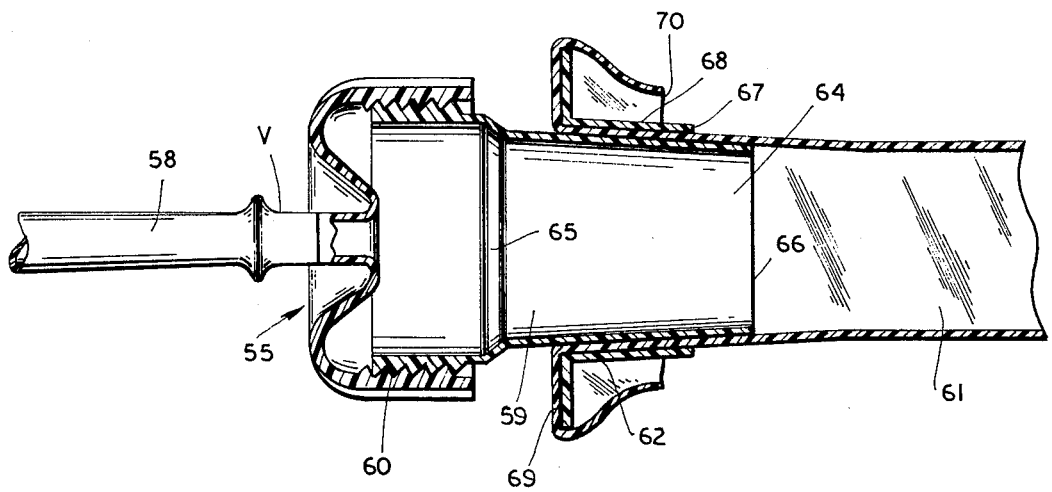
FIG. 6 is a cross-sectional view taken substantially along the line 6—6 in FIG. 5.

Referring now to FIGS. 5 and 6 of the drawings, there is disclosed an embodiment of the invention which includes the valve V, substantially as shown in FIG. 2, and a cap which is as flexible as the cap shown in FIG. 4 of the drawings. The cap of this embodiment, however, is somewhat different from the cap 36 of FIG. 4. In FIGS. 5 and 6, the cap is designated generally at 55, and the cap includes web 56 to allow motion of the nozzle 58. Also, in this embodiment, tubular body 59 is similar to tubular body 14, formed with external threads 60 for mating with complementary threads of the inside of cap 55. However, in this embodiment, to clamp the flexible bag 61 to the tubular body 59, there is provided a wedge ring 62.

Tubular body 59 is formed with a bag receiving section 64 that is tapered inwardly to produce a frustoconical shape. Wedge ring 62 includes a sleeve 68 having a complementary frusto-conical shape with the angle thereof being substantially the same as the angle for the bag receiving section 64. Extending outwardly from the enlarged end of the sleeve 68 is a circular flange 69.

In order to assemble the syringe of this embodiment, the open end of a bag 61 is passed through sleeve 68, and the edge 70 of the open end of bag 61 is reversed and passed over flange 69 to lie adjacent sleeve 68. With bag 61 so installed, the bag receiving section 64 is pushed through the wedge ring 62, and the wedge ring 62 is urged along the bag receiving section 64 with a slight twisting motion until there is a tight wedged fit to hold the bag in position. When assembled, the lower end 66 of bag receiving section 64 extends beyond the lower end 67 of sleeve 68. The apparatus may then be used as previously described for other embodiments of the present invention. Bag 61 should extend beyond the end 66 of section 64 for a substantial length so that the bag may be grasped and squeezed to pump liquid from the bag.

Figure 7:
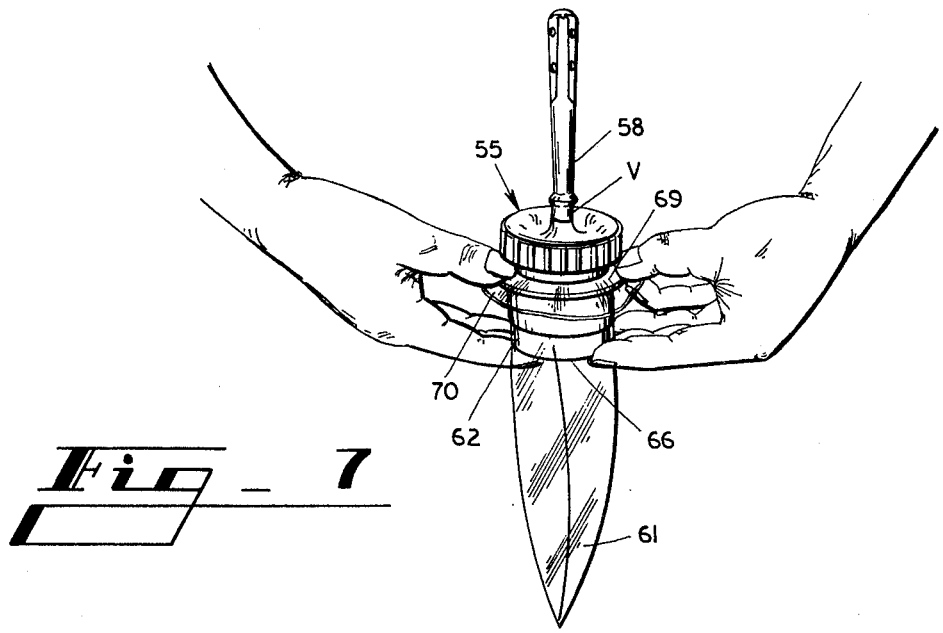
FIG. 7 is a perspective view of the device shown in FIGS. 5 and 6 illustrating the method for removing the clamping means.

When the syringe has been used, and it is desired to remove the bag 61 from the body 59, the removal can be easily accomplished as shown in FIG. 7. By positioning the thumbs of the hands on the flange 69 and one or more fingers of each hand at the end 66 of the section 64 and squeezing the fingers toward the thumbs, the bag receiving section 64 may be removed from within the sleeve 68. In this position, a person's grip can be used to urge the wedge ring towards the smaller end of the bag receiving section 64 for easy removal of the bag.

With the above discussion in mind, it should now be understood that the syringe of the present invention provides a very simple structure whereby a flexible bag is utilized as the body member of a syringe. The flexible bag 11 or 61 may be packaged with a dry chemical therein and also may be folded flat for easy packaging and storage in a sterile condition. When one desires to use the syringe, the flexible bag 11 or 61 would be opened and appropriately fixed to the tubular body 14 or 59. At this point, water or other liquid is placed into the bag and the cap 16, 36 or 55 is secured to the end of the tubular body, being sure that the valve V is closed at the time the cap is placed on the body. The syringe is now ready for use, and there is no possibility of an inadvertent dispensing of the liquid since the valve V is closed and the flexible bag is securely locked to the cap.

After insertion of the nozzle, the valve V is opened by simply moving the nozzle outwardly with respect to the cap and liquid flows from the bag, through the cap, through valve V and to the nozzle. The flexible connection between the nozzle 12, 32 or 58 and the cap 16, 36 or 55 allows a certain flexibility in use of the syringe in a self-administered treatment such as a self-administered douche or a self-administered enema. Furthermore, the entire device is so designed that is can be manufactured very inexpensively but efficiently for its intended purpose. Additionally, the cap may be sold with a plurality of different nozzles so that the same syringe may be used for a douche, an enema, or a general flooding treatment of eyes, ears and the like.

It will, of course, be understood by those skilled in the art that the particular embodiments of the invention are here presented by way of illustration only and are meant to be in no way restrictive; therefore, numerous changes and modifications may be made and the full and equivalents resorted to without departing from the spirit or scope of the invention as defined in the appended claims.

What is claimed is:

1. A disposable syringe, including a flexible bag, a cap, means for releasably fixing said plastic bag with respect to said cap for communication of the interior of said bag with the interior of said cap, said cap defining an opening therein in communication with the interior of said cap and a nozzle in communication with said opening, said syringe further including a tubular body, means for selectively fixing said cap to a first end of said tubular body, said tubular body having a frustoconical portion for receiving said flexible bag thereover, and means for releasably fixing said flexible bag to said frustoconical portion including a wedge ring receivable over said flexible bag.

2. A disposable syringe as claimed in claim 1, said wedge ring comprising a sleeve concentric with said frustoconical portion for engaging said flexible bag, and a circular flange extending from said sleeve, said sleeve being so constructed and arranged that when said sleeve is urged along said frustoconical portion with said flexible bag therebetween said sleeve is wedged into a locking condition.

3. A disposable syringe comprising a flexible and readily foldable bag having fluid retaining properties and sized so as to be readily grasped and squeezed for the administration of a fluid contained within the bag, said bag having an open end of a predetermined size, a tubular body engaging said open end of said bag in axially overlapped relation, a cap member releasably secured to said tubular member, a valve portion mounted on said cap, said valve portion including a central opening therein in communication with the interior of said cap member, an elongated nozzle including a nozzle extension integrally formed therewith, said nozzle extension being receivable over said valve portion to form a fluid flow control valve, said cap member having an outer circumferential flange, said tubular body having an axial length in excess of the axial length of said flange of said cap, but substantially less than the axial length of said flexible bag, and wherein the syringe includes a wedge ring positioned over a lower end of said tubular body, the portion of said bag adjacent to the open end thereof lying between said wedge ring and said tubular body.

4. Disposable syringe of claim 3 wherein said cap includes a flexible central area and said valve portion is integrally joined to said flexible central area.

5. Disposable syringe of claim 3 wherein said valve portion and said nozzle extension cooperate to form a fluid flow control valve which is actuated by longitudinal movement of said nozzle extension with respect to said valve portion to selectively permit flow of fluid from said flexible bag through said cap and said central opening within said valve portion, and then through said flow control valve and through said nozzle extension and nozzle.

* * * * *